US006332100B1

(12) United States Patent
Sahai et al.

(10) Patent No.: US 6,332,100 B1
(45) Date of Patent: *Dec. 18, 2001

(54) APPARATUS AND METHOD FOR MEDICATION DISPENSING AND MESSAGING

(75) Inventors: Anil Sahai, Webster City, IA (US); Stephen K. Brede, Merrimack, NH (US); Douglas A. Topliffe, Mount Vernon, NH (US); Roger Ogden Topliffe, Sunapee, NH (US)

(73) Assignee: Interactive Medical Developments, L.C., Webster City, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/412,575

(22) Filed: Oct. 5, 1999

Related U.S. Application Data

(63) Continuation-in-part of application No. 09/046,644, filed on Mar. 24, 1998, now Pat. No. 5,971,594.

(51) Int. Cl.[7] .................................................... C06F 17/00
(52) U.S. Cl. ......................... 700/242; 700/236; 700/244
(58) Field of Search ................................... 700/242, 236, 700/244

(56) References Cited

U.S. PATENT DOCUMENTS

| | | |
|---|---|---|
| 4,223,801 | 9/1980 | Carlson . |
| 4,682,299 * | 7/1987 | McIntosh et al. ................... 364/569 |
| 4,695,954 | 9/1987 | Rose et al. . |
| 4,725,997 | 2/1988 | Urquhart et al. . |
| 4,768,177 | 8/1988 | Kehr et al. . |
| 4,837,719 | 6/1989 | McIntosh et al. . |
| 4,872,591 * | 10/1989 | Konopka ................................ 221/3 |
| 4,970,669 | 11/1990 | McIntosh . |
| 5,020,037 | 5/1991 | Raven . |
| 5,047,948 * | 9/1991 | Turner ................................. 364/479 |
| 5,088,056 * | 2/1992 | McIntosh et al. ................... 364/569 |
| 5,159,581 | 10/1992 | Agans . |
| 5,200,891 | 4/1993 | Kehr et al. . |
| 5,329,459 | 7/1994 | Kaufman et al. . |
| 5,347,453 | 9/1994 | Maestre . |
| 5,392,952 | 2/1995 | Bowden . |
| 5,412,372 | 5/1995 | Parkhurst et al. . |
| 5,431,299 | 7/1995 | Brewer et al. . |
| 5,522,525 | 6/1996 | McLaughlin et al. . |
| 5,562,232 | 10/1996 | Pearson . |
| 5,564,593 | 10/1996 | East, Sr. . |
| 5,582,323 | 12/1996 | Kurtenbach . |
| 5,609,268 | 3/1997 | Shaw . |
| 5,641,091 | 6/1997 | Daneshvar . |

(List continued on next page.)

FOREIGN PATENT DOCUMENTS

| | | | |
|---|---|---|---|
| 11-39445 * | 2/1999 | (JP) ................................. G06K/19/00 |
| WO 97/04734 * | 2/1997 | (WO) ................................ A61J/7/04 |

*Primary Examiner*—Christopher P. Ellis
*Assistant Examiner*—Michael E. Butler
(74) *Attorney, Agent, or Firm*—Patton Boggs LLP

(57) ABSTRACT

A medication dispensing system comprising a programmable on-site medication dispensing unit and a central monitoring facility. The on-site medication dispensing unit holds medication in a plurality of canisters which it selects from according to an entered and stored prescription regimen and then notifies the patient by an audible or other sensory signal. If the patient presses a button within a prescribed time, the unit dispenses the selected canisters. If the patient does not press the button within the prescribed time, or if the unit detects a failure to dispense the selected canister, the unit makes the canister inaccessible and contacts, in order, a predetermined list of caregivers and then a central monitoring facility. An audio message is downloaded from the central monitoring facility to one or more of the on-site dispensing units, and played in accordance with a downloaded play program.

10 Claims, 11 Drawing Sheets

U.S. PATENT DOCUMENTS

| | | |
|---|---|---|
| 5,646,912 | 7/1997 | Cousin . |
| 5,657,236 | 8/1997 | Conkright . |
| 5,752,621 * | 5/1998 | Passamante ............................ 221/13 |
| 5,827,180 * | 10/1998 | Goodman .............................. 600/300 |
| 5,971,594 * | 10/1999 | Sahai et al. ..................... 364/479.12 |
| 5,988,858 * | 10/1998 | Yuyama et al. ................. 364/478.16 |

* cited by examiner

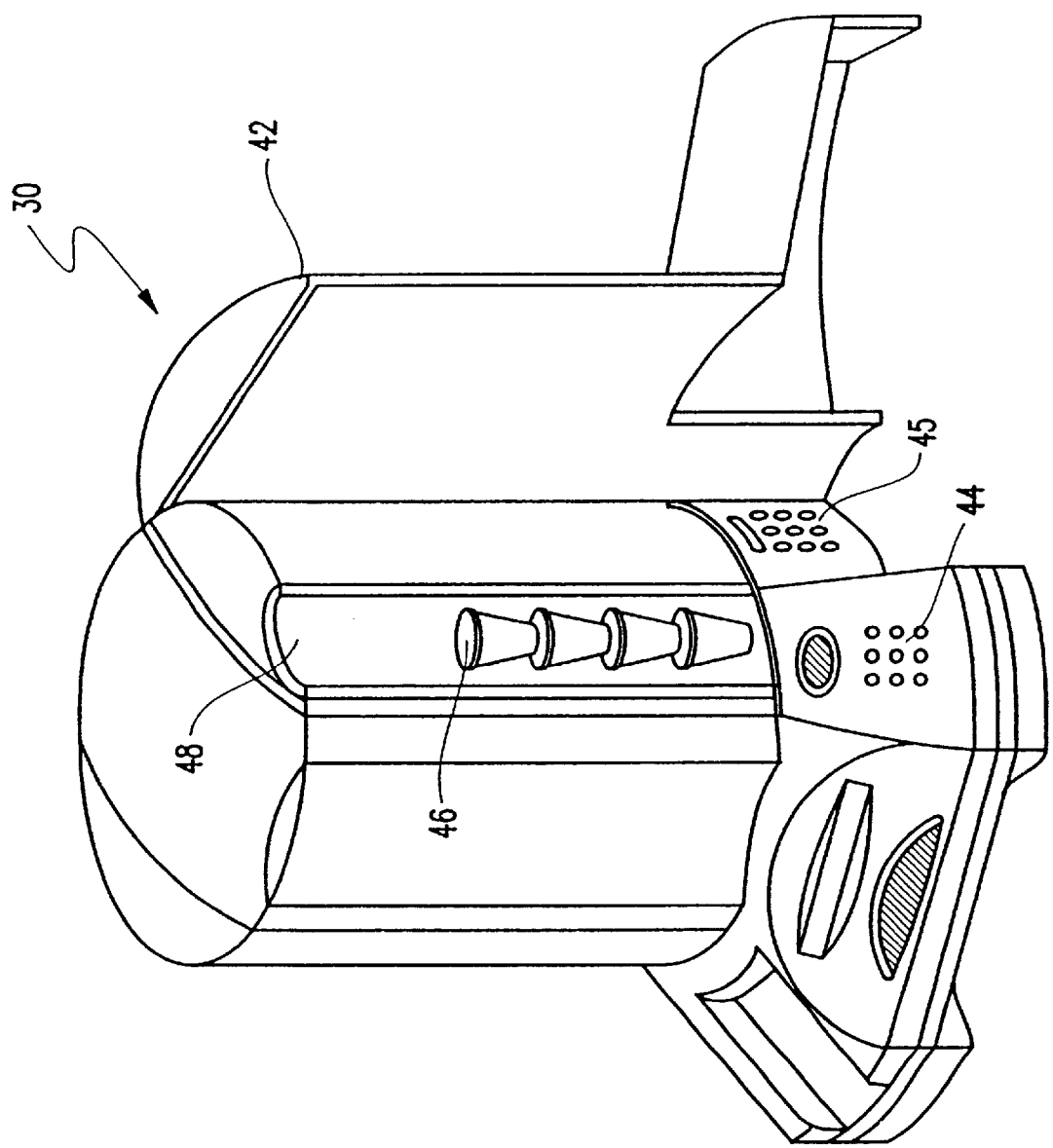

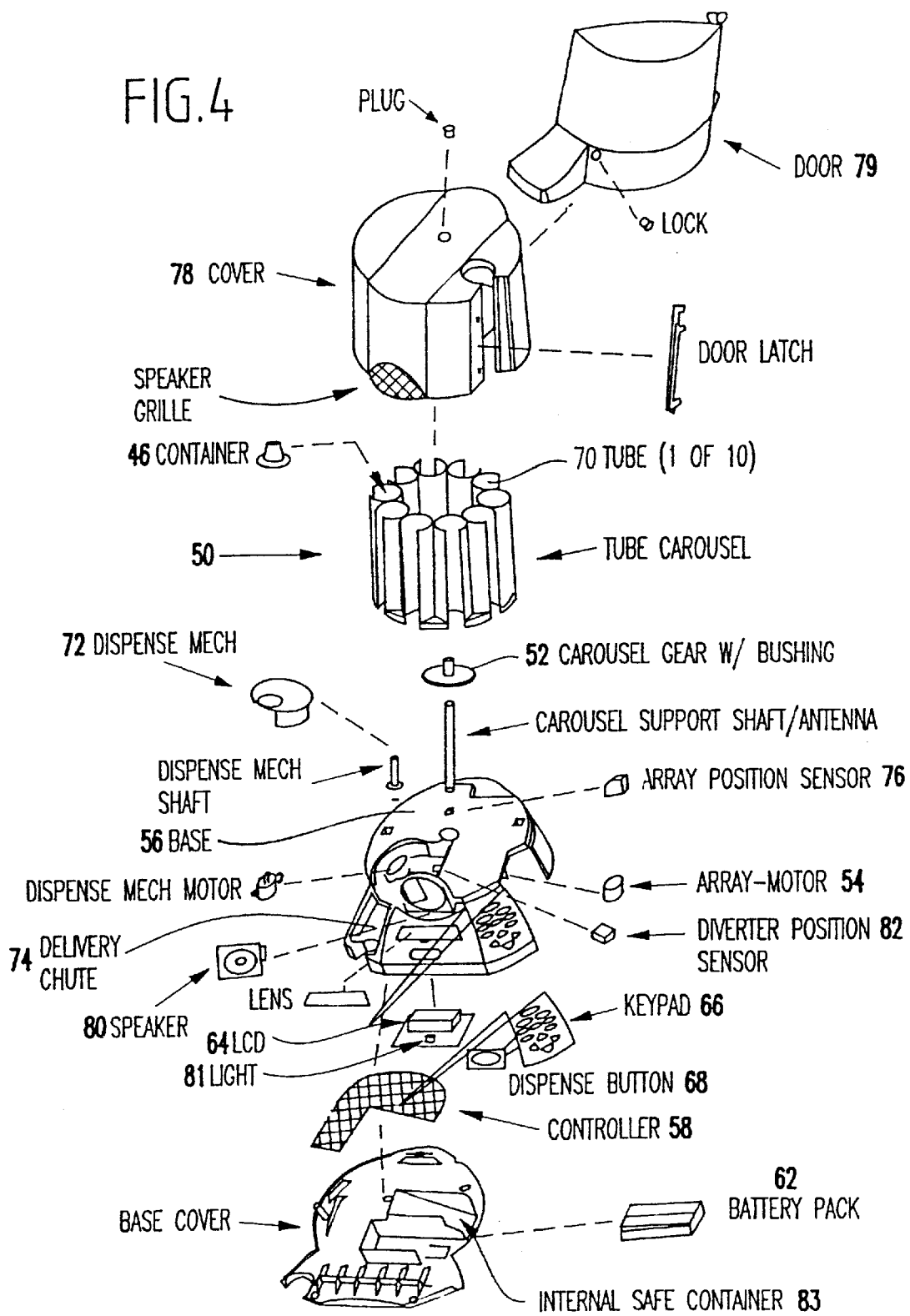

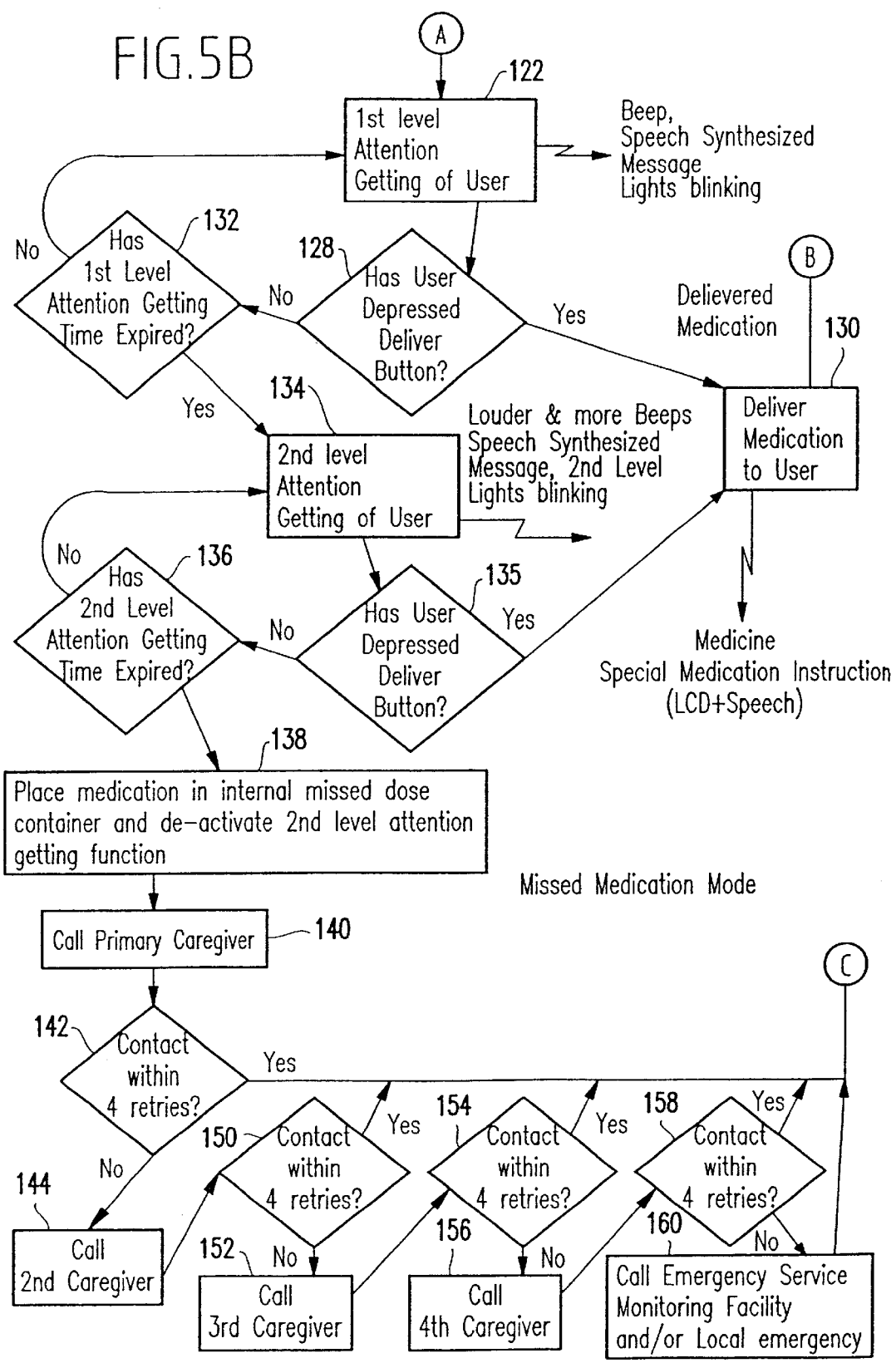

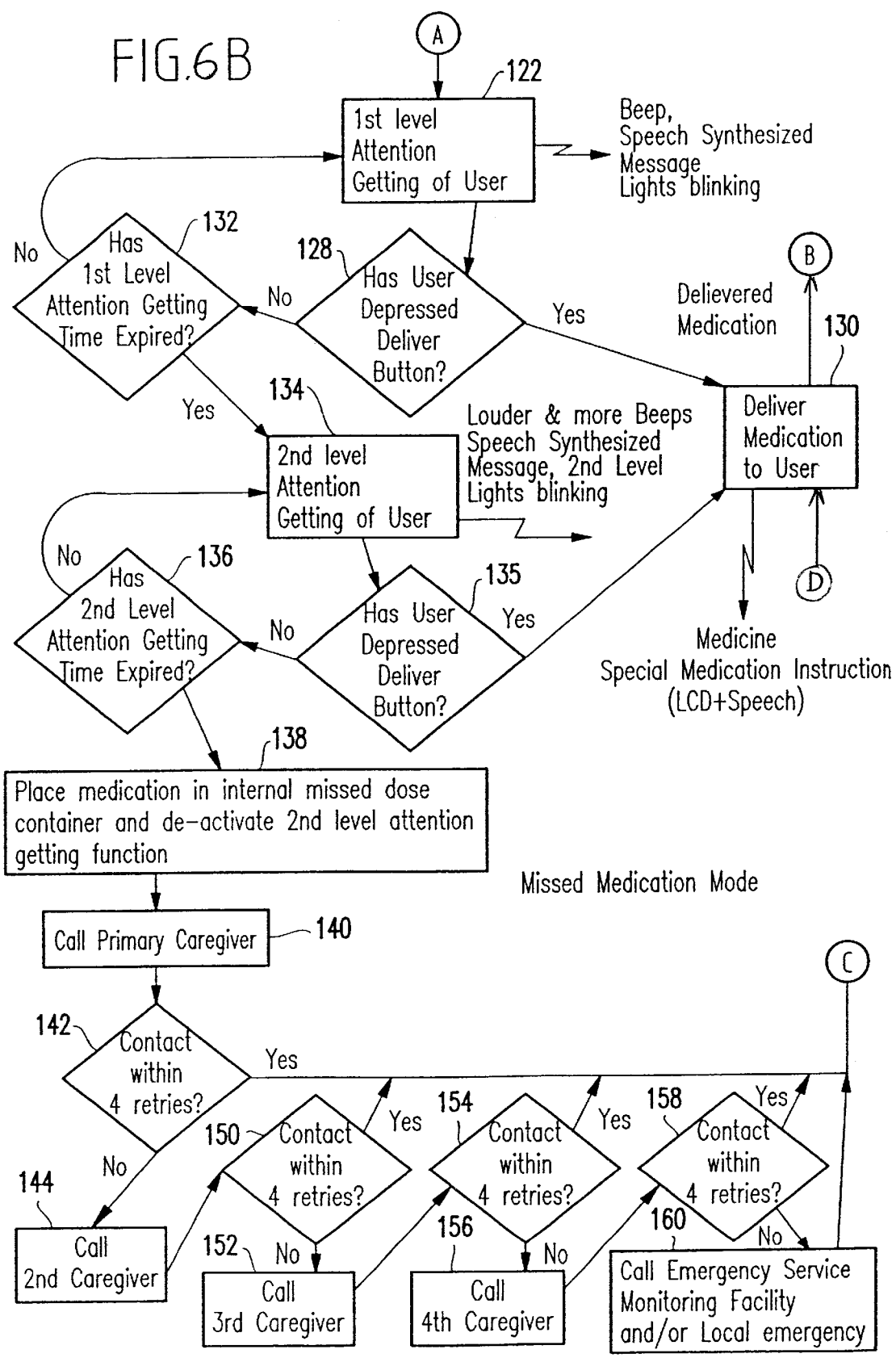

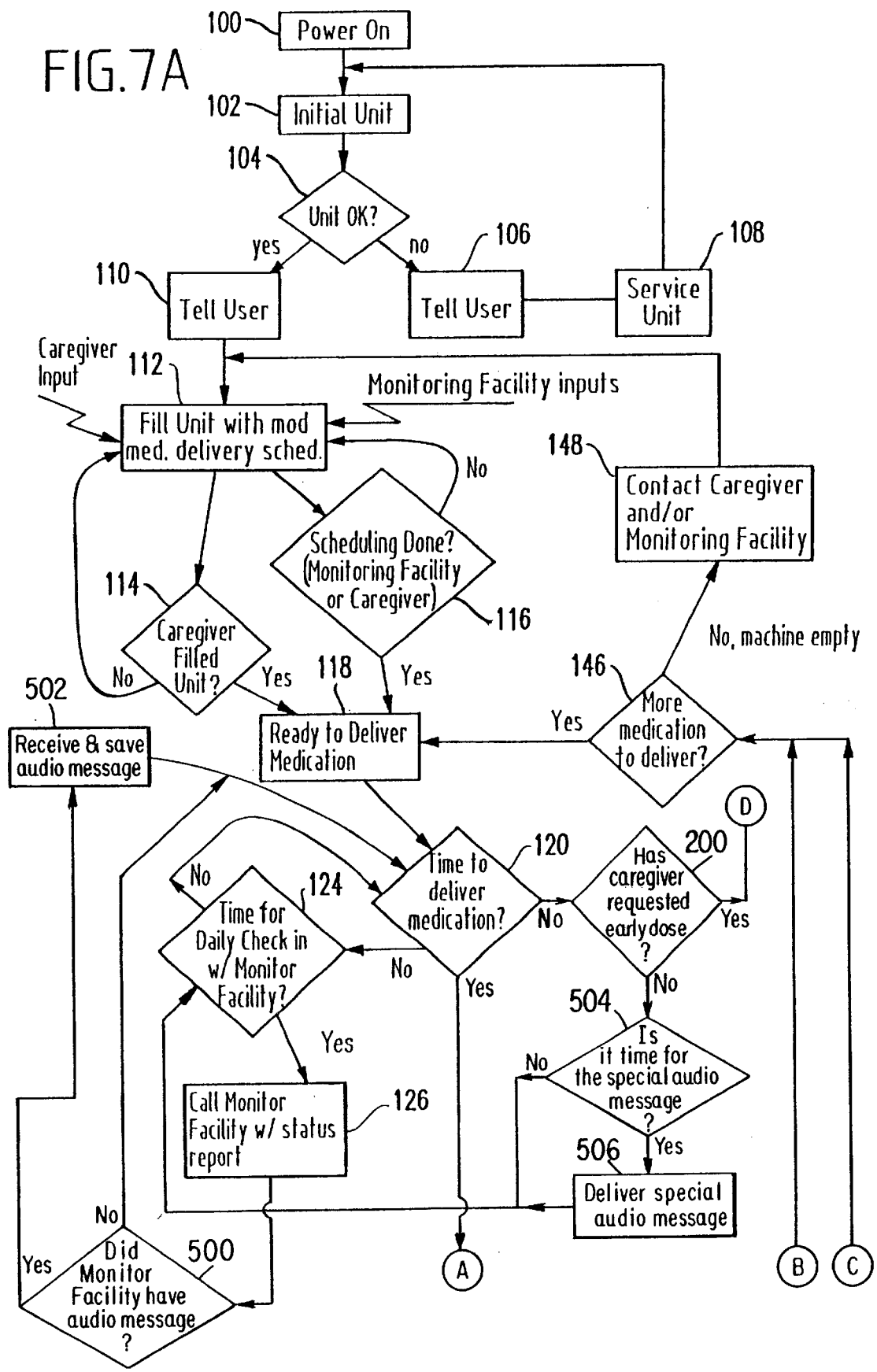

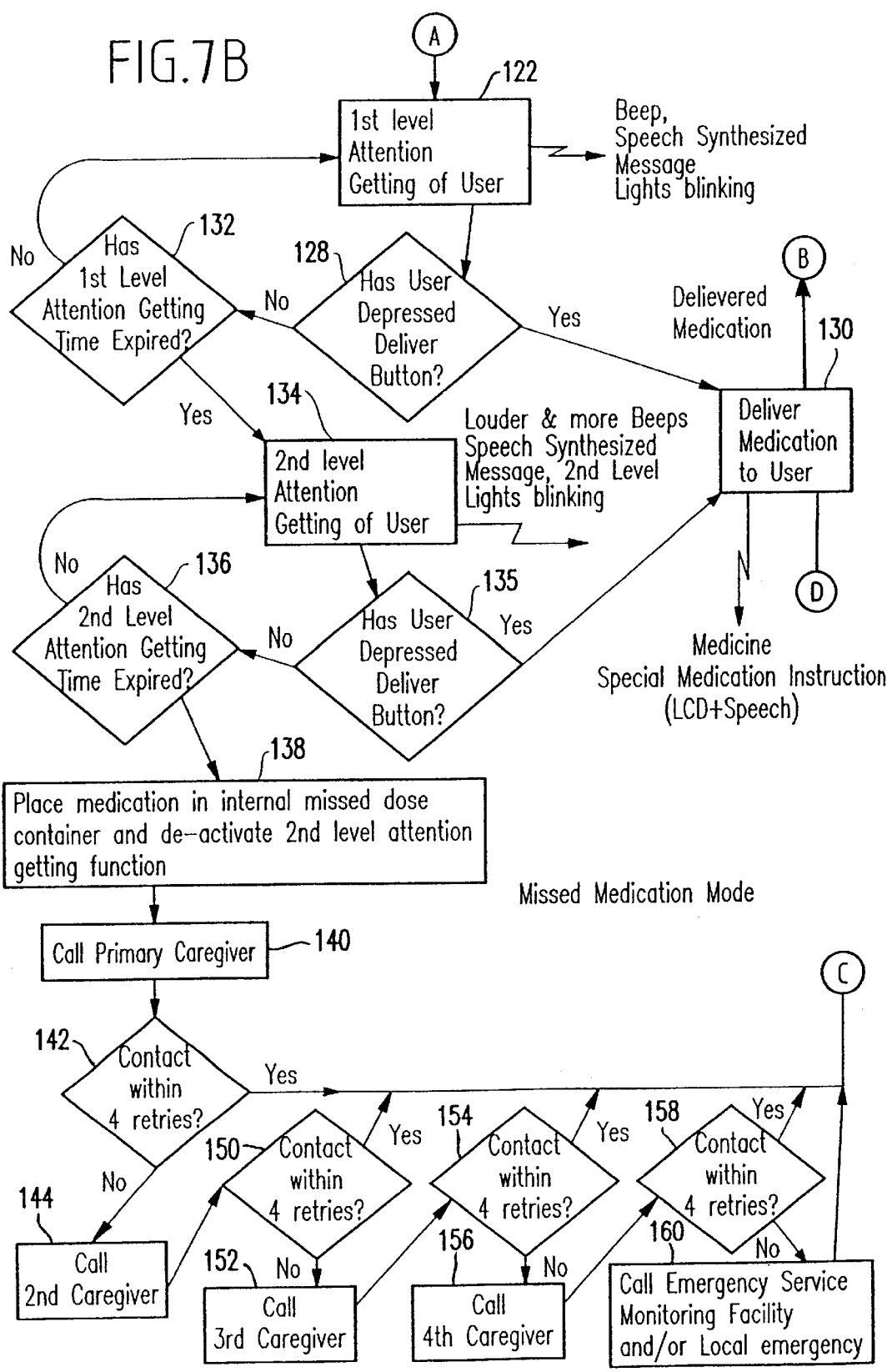

APPARATUS AND METHOD FOR MEDICATION DISPENSING AND MESSAGING

RELATED APPLICATIONS

This application is a continuation-in-part (CIP) of U.S. patent application Ser. No. 09/046,644, entitled "Medication Dispensing System", filed Mar. 24, 1998 now U.S. Pat. No. 5,971,594.

DESCRIPTION

Background of the Invention

1. Field of the Invention

The invention is generally related to a medication dispensing unit, and more particularly to a device that dispenses medication, monitors compliance with a medication regime, and provides voice messaging through the dispensing unit.

2. Description of the Related Art

Doctors commonly prescribe a regimen of pills to be taken by ill persons. For example, a regimen such as "take two of the blue pills every six hours and one of the green pills every four hours" or the like is not uncommon. For some persons, such a specific regimen or course of medication may be easily followed. For other persons however, confusion can arise both concerning the schedule and concerning whether or not the medication has been taken. This problem occurs frequently with elderly persons who may have suffered some loss of mental faculties, but can occur with other persons as well.

A variety of automated dispensers of pills which are purportedly aimed at some aspects of this dispensing problem are described in the related art. According to their respective descriptions these dispensers are intended to provide for dispensing of pills according to some specified regimen. In addition, in some cases, they have some described means to permit a determination of deviations from their programmed regimen. These dispensers, however, have shortcomings in their complexity, cost, flexibility, ease of use, error resistance for use in many conventional medication dispensing needs.

For example, U.S. Pat. No. 5,582,323 issued to Kurtenbach describes a medication dispenser and monitor system. According to its description, the Kurtenbach dispenser apparatus has a plurality of compartments which directly receive and hold pills for dispensing individual medication dosages. The dispenser provides an alarm alerting the patient that it is time to dispense his or her medication. If the medication is not dispensed the unit makes a call to a monitoring facility. The medication dispensing and monitoring system described in Kurtenbach also allows for recording non compliance by the patient.

However, Kurtenbach does not provide any protection against overdosing by the patient and, further, does not provide any emergency communication to a local caregiver who is more likely to quickly aid the patient than the central monitoring service. Also, the described medication apparatus directly stores pills in compartments which may become contaminated by residue.

U.S. Pat. No. 5,646,912 issued to Cousin also describes a medication dispensing apparatus. According to its description the apparatus has a plurality of pill dispensing units controlled by a microprocessor that is programmed with a patients medication schedule. According to its description, the pill dispensing apparatus can prevent overdosage or underdosage in the subject patient by altering the medication dosage dispensing schedule.

Cousin, however, has shortcomings which could render it inadequate for many anticipated uses. One shortcoming is that its apparatus uses compartments that directly contain the medication to be dispensed, and such compartments are readily susceptible to residue build up. Additionally, Cousin's described scheme and apparatus for preventing overdosage or underdosage in a subject patient is complicated and, accordingly, could be difficult to implement.

There is therefore a need for an improved dispensing system for home medication. The present invention is directed to this need, and provides further related advantages.

SUMMARY OF THE INVENTION

It is an object of this invention to provide an on-site medication dispensing unit that is readily programmable for dispensing pills to a patient over an extended period of time and which monitors patient compliance with the programmed medication regime.

Another object of this invention is to prevent overdosage or stacking of dosages in the unit's output mechanism by having a visual and/or audible alerting feature which notifies the patient at a prescribed dosage time in accordance with the regimen that is programmed into the unit, and then having a limited time window during which the patient must press a button or similar input device to activate the unit's output mechanism to effect a physical dispensing of the canister from the unit. The time window is re-programmable. If the patient has not pressed the button or otherwise activated the input device when the time window ends, the canister is dropped into an inaccessible bin located within the unit. A further feature of the unit alerts the patient in steps of escalating intensity, either audibly and visually, or both, if the button or similar input device is not activated.

It is another object of this invention to provide a medication dispensing unit which is linked to a 24 hour monitoring facility, whereby the monitoring facility can alert a caregiver if an occurrence that is defined by the unit's program to be an emergency situation arises. An example emergency situation is the patient's failure to activate the dispensing button which, as described above, causes the canister to be dropped to an inaccessible bin, more than a predetermined number of times over a predetermined time duration. Another example emergency situation is a failure of the on-site dispensing unit, upon detection by the unit's self-test features described herein.

It is still another object of the present invention to provide an automatic prioritized order of contacting persons in the event of the on-site unit detecting an emergency situation. Pursuant to this object, according to one example embodiment, the on-site dispensing unit first responds to the detection of an emergency by placing a telephone call to a first designated local caregiver such as, for example, a relative of the patient. An example response from the caregiver who is contacted consists, for example, of the caregiver pressing a telephone key, or sequence of keys, programmed to be recognized by the on-site dispensing unit. If the first designated local caregiver is not reachable or does not respond to the call, the on-site unit then contacts, in sequence, a second, third and fourth designated local caregiver until one of them responds. If none of the designated caregivers respond to the on-site dispensing unit's calls, the on-site unit contacts the central monitoring facility. The central monitoring facility then responds in a manner such that described for the example embodiment, with variations set according to design choice. One response is, for example, to contact the local authorities. One benefit of the prioritized calling feature is that local caregivers, who can readily proceed to the patient's location, are notified first. Another benefit is a reduction in the frequency that the central monitoring facility notifies the authorities.

As described above, the present invention provides for monitoring of the patient's compliance with a prescribed medication regimen by alerting one or more caregivers and the central monitoring facility if a dosage is missed. A further contemplated feature is a periodic reporting by the dispensing unit to the central monitoring facility of a history of the unit's activity. Examples of the reported history include: each dosage alert, each depressing of the unit's dispensing button, each detection of a canister being fully dispensed from the unit, and each missed dosage. A still further contemplated feature of the history reporting function is for the on-site unit to receive a request-for-report signal from the central monitoring facility, the request being for either an entire activity history, or for a specific subset of the activity, as well as a report of the current dosage regimen that is programmed into the unit.

A further embodiment of the invention provides the central monitoring facility of the above embodiments with a record keeping function which, in addition to a record stored in the dispensing unit, records the patients compliance with the prescribed medication dosage regimen. This record is available to the caregiver or patient physician from the central monitoring facility.

A further embodiment of this invention combines an early dose capability with the program regimen dispensing of the above embodiments. In this embodiment, the on-site dispenser has an added programmability feature by which the caregiver, by entering appropriate commands into a user-interface of the on-site unit, can obtain an early dispensing of one or more doses of the patient's medication. An example circumstance requiring this early dispensing would be the patient taking a day trip, during which time medication would still be needed, regardless of the patient being remote from the on-site dispensing unit.

A still further embodiment of this invention comprises a remotely programmable audio message system which includes a message content input and a message program command input located at, for example, the central monitoring facility of the above embodiments, and a message receiving input and audio generation unit installed in, or connected to, the on-site dispensing unit. An example message content input includes a microphone, an A/D converter, and digital formatting unit. The message is spoken into the microphone, digitized, and formatted for transmission to the on-site dispensing unit. A command is entered into the message program common input specifying, for example, which one(s) of a plurality of on-site dispensing units are to receive the message, the time(s) and/or event(s) at which the speaker unit of the designated on-site dispensing unit(s) would generate the message. An example message would remind a patient, by the generated or replayed speech signal, to take a medication which is not dispensed by the unit, or about a doctor's office visit, or to take precautions against a currently circulating communicable disease.

One embodiment of the on-site medication dispenser unit includes a rotating tube rack wherein the tubes may be loaded with at least a weeks worth of a particular type of medication or types of medication. When a medication dosage is to be dispensed, the tube rack is rotated so that the proper tube is positioned at a dispensing chute. At the prescribed dosage time the dispenser's program initiates an alert to the patient. As described above, when the patient is alerted, he or she is required to push a dispensing button within a programmable time window. If the button is pushed the aligned tube of the rotating mechanism releases the bottom-most canister (dispensing cup), which then drops into a chute accessible to the patient.

If the patient does not dispense the medication when alerted to do so, the dispenser first, for some embodiments, steps through a progressive alerting of audio (tones and pre-recorded voice messages) and visual alerts with increasing intensity, and if the medicine is not dispensed, the rotating tube mechanism drops the canister into an inaccessible bin and the unit attempts to contact, in order, a pre-programmed list of caregivers and then if not successful, notifies the 24 hour central monitoring facility.

According to one example embodiment, the on-site dispensing unit is loaded by first filling the appropriate plurality of canisters, or dispensing cups with the individual medication dosages, then transporting the filled canisters to the on-site unit, and loading them into the dispensing mechanism's tubes in the order in which they are to be dispensed. The plurality of canisters or dispensing cups can be loaded, and the dispensing units controller programmed accordingly, to provide either a large number of doses per day for up to, as an example, a week at a time, or for a smaller number of doses per day over multiple weeks. The canisters or dispensing cups may be filled at the location of the on-site unit, or pre-filled at a central distribution facility, or at a local station, such a place within a nursing home.

After loading the canisters into the tubes, the unit is programmed using one of the following three methods: (i) call the central monitoring facility and have the unit programmed remotely, (ii) use a setup panel to select a pre-programmed standard, and (ii) use a setup control panel to enter in a customized schedule.

A control panel for programming the dispensing unit is preferably located under a cover of the dispensing unit, thereby preventing accidental or other altering of the stored medication dosage schedule.

In addition to the medication dispensing and monitoring functions of the dispensing unit, a further embodiment includes a wireless communicating device worn by the patient which is communicatively linked with the dispenser to provide additional emergency protection to some patients. In an emergency, the patient activates the wireless communication device, which would then communicate with the dispensing unit. The dispensing unit would in turn send an emergency message to the central monitoring station. The personal communication device may be a pendant worn around the neck, or any other suitable device that can be worn on the patient's body. The medication dispensing unit may optionally incorporate and emergency button that serves the same function as the personal communication device. Other embodiments of the wireless emergency communications device are a wall mounted wireless emergency button and a table top wireless emergency button.

BRIEF DESCRIPTION OF THE DRAWINGS

The foregoing and other objects, aspects and advantages will be better understood from the following detailed description of the preferred embodiments of the invention with reference to the drawings, in which:

FIG. 3 is an isometric view of the FIG. 2 on site medication dispenser with the cover panel open;

FIG. 4 is an exploded isometric view of the FIG. 2 on-site medication dispenser;

FIGS. 5A and 5B show a detailed operational flow chart for an on-site dispensing unit and monitoring system according to the present invention;

FIGS. 6A and 6B are an operational flow chart of an early dosing feature for combination with the apparatus and operation depicted by FIGS. 1–4, 5A and 5B;

FIGS. 7A and 7B are an operational flow chart of a messaging service feature for combination with the operational flow chart of FIGS. 5A and 5B.

DETAILED DESCRIPTION OF THE PREFERRED EMBODIMENTS OF THE INVENTION

Figure 1:
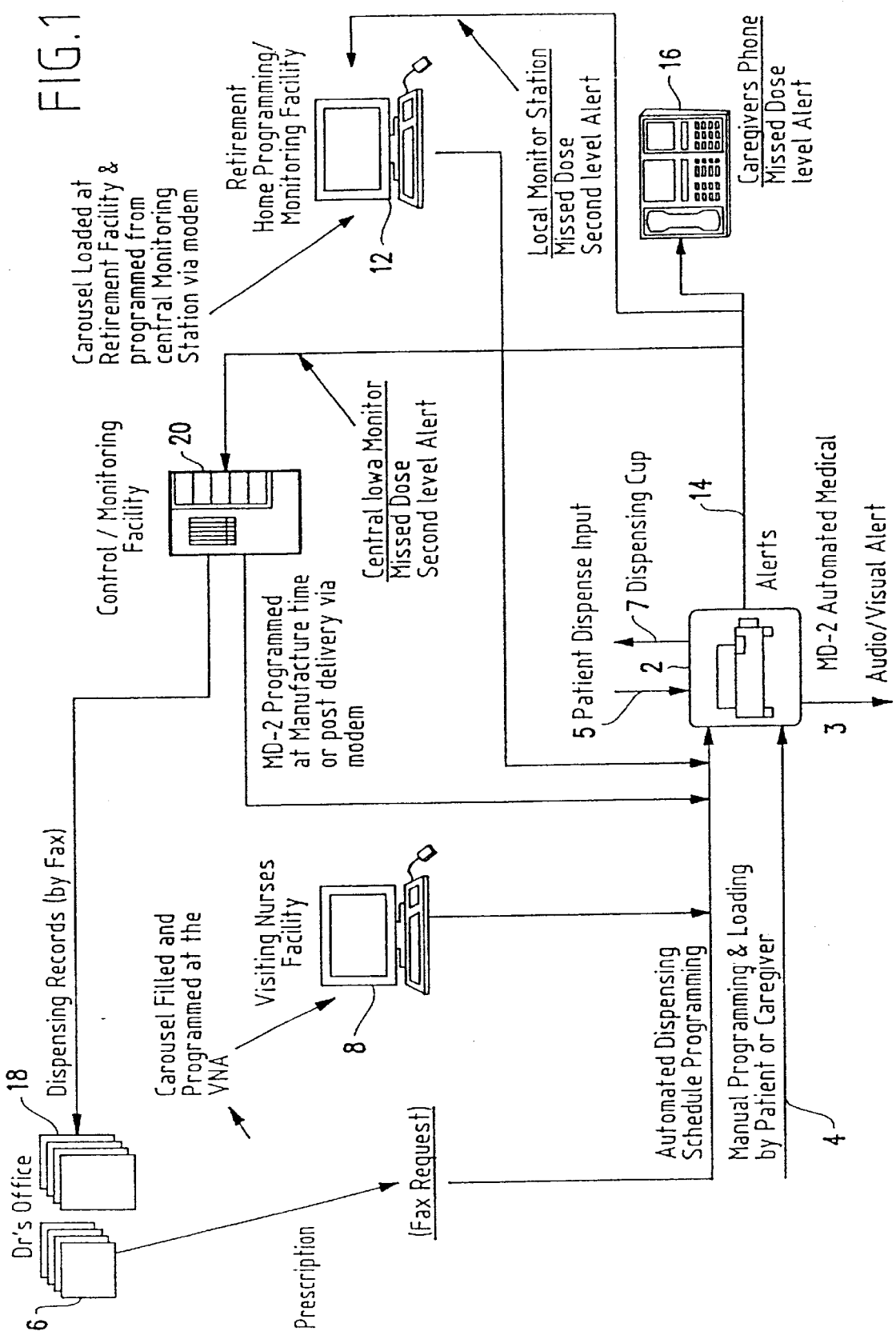
FIG. 1 is a high level system diagram of a medication dispensing and monitoring system according to the present invention.

FIG. 1 is a high level system diagram of an example medication dispensing and monitoring system according to the present invention. The FIG. 1 system includes an on-site medication dispenser 2 which stores a plurality of canisters or dispensing cups, described in detail further below, each cup filled with one or several pills of one or more type for dispensing at a prescribed time. The canisters or dispensing cups are loaded into the on-site dispensing unit 2 by authorized persons from a visiting nurse facility or from a doctor's office, or by a local caregiver. The specific apparatus and details of operation of the medical dispensing unit 2 are described further below in reference to FIGS. 2–4, 5A, and 5B.

The on-site dispensing unit 2 has a microprocessor-based controller (shown in FIG. 4), which is described further below, the controller having standard digital data storage features (not shown) both for data and for the controller programs (not shown). The dispenser unit 2 data storage receives and stores a dispensing program, or receives data entries into a prestored user-prompt program, representing the patient's prescribed medication regimen. The program or data is entered into the unit 2 manually, by either the patient or the caregiver 4, or is received via modem (not shown) from one of several remote sites including the patient's physician's office 6, a nursing facility 8, a central control/monitoring facility 20, or a retirement home facility 12. The on-site dispensing unit 2 then, by the example apparatus and operation described below, executes the entered dispensing program by alerting the patient, by a visual and/or audible means 3, at each of the programmed dosing times and, concurrent with each alerting operation, places or assigns one of its internally stored dispensing cups into a ready-to-dispense mode or mechanical state. The controller concurrently establishes a window of time, relative to the alerting signal, during which the patient can input a dispensing signal 5 via, for example, a button, shown as item 68 in FIG. 4, or other input device, such as a touchscreen (not shown). The duration of the time window is set by the entered program or by a default value.

If the user input signal 5 is received before expiration of the time window the assigned dispensing cup is output from the unit, as shown by label 7 and as described in further detail below.

If the patient has not yet responded, e.g., pushed the button 68 of the medication dispensing unit 2, at the end of the time window, the unit 2 of the FIG. 1 embodiment immediately transmits an alert 14 via, for example, a unit modem (not shown) to a first designated caregiver 16. In addition to generating the alert 14, the on-site dispensing unit 2 drops the dispensing cup (which had been in the ready-to-dispense mode) into an inaccessible storage of the unit 2, as described in more detail further below.

If no response is received by the unit 2 from the first designated caregiver, the unit 2 sends another alert 14 to a second designated caregiver (not shown) or, if there is no designated second caregiver, to the retirement/nursing home monitoring facility 12 (if the patient is in a retirement home environment). Referring to FIG. 1, a preferred example notifies the central monitoring facility that there is no valid response from any of the designated caregivers 16 or from the retirement home monitoring facility 12. The alerting sequences presented above is for purposes of example only, and different sequences are readily identified by one of ordinary skill upon reading this disclosure, and the associated program can be readily written into the dispenser unit 2 microprocessor-based controller. As an alternative to the unit 2 modem (not shown), communication with the remote sites, such as 16, 12 and 20, can be realized by direct a phone line or cellular phone connection. Regarding the specific form of receipt verification signal that the remote monitoring sites 16, 12 and 20 transmit back to the on-site dispensing unit 2, this is a design choice based on preference. Examples include a specific phone keypad (not shown) entry, or sequence of entries, or a designated key (not shown). Further, the dispenser unit 2 may be equipped with a voice-recognition feature, recognizing, for example, "I'll be right over" being received in response to calling the designated caregiver's telephone. Various commercial voice recognition hardware/software modules, which are readily incorporated into a standard microprocessor based controller, are available as off-the-shelf items.

In the description above of the FIG. 1 example system, the on-site dispensing unit immediately transmits an alert signal 14 if there has been no user input of the dispensing signal when the time window ends. A further embodiment, which is described below in reference to FIGS. 5A and 5B, uses a plurality of, for example, two time windows during which the user may input the dispensing signal, e.g., press the button 68. In that further embodiment, the audio or visual alarm is generated at a first intensity during the first time window. If that first time window ends and the user has not yet entered a dispensing signal the unit increases the alarm level. The increased alarm level is continuous or, alternatively, is steadily increasing, until the end of the second time window. If the user, at the end of the second time window, has still not entered the dispensing signal then the unit 2 generates the alert signal 14 as described above.

As described above, and referring to FIG. 1, the central monitoring facility 20 is connected to the on-site medication dispenser 2 via, for example, a modem (not shown). In a further embodiment, addition to the central monitoring facility receiving alerts 14 from the unit 2, unit 2 periodically reports the unit's operation and status to the central monitoring facility 20. The information transmitted by this periodic reporting is a design choice including, for example, a history of all dispensing operations over a set time period. In a further embodiment, which may be combined with the above-described periodic reporting function, the central monitoring facility sends queries (not labeled) to the on-site dispensing unit 2, via the modem line, requesting information. Still further, the patient's physician's office 6 may request a record 18 of dosage schedule compliance from the central monitoring facility 20 to further enhance the treatment of the patient.

Figure 2:
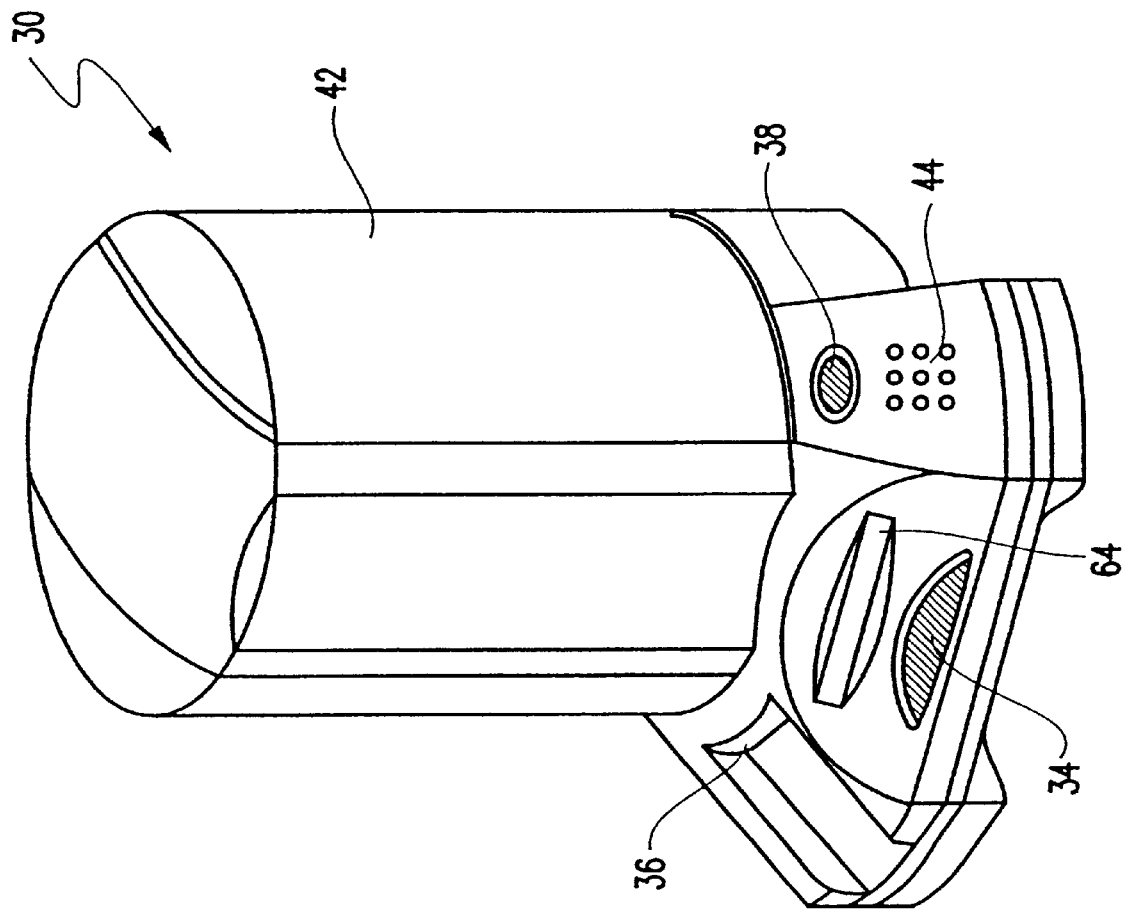
FIG. 2 is an isometric view of an on-site medication dispenser according to the present invention.

FIGS. 2–4 show as item 30 one example embodiment of the on-site medication dispenser 2 according to the present invention. For purposes of this description, references to the example on-site dispensing unit 30 of FIGS. 2–4 refer also to the dispensing unit 2 within the system shown by FIG. 1.

Referring to FIG. 4, the unit 30 has a LCD display 32 which displays information describing the medication dosage schedule to the patient, as well as other information that can assist the patient with the administering of a medication. An example of other such information is that when a specific medication is dispensed, the display may, if appropriate, indicate that the medication should be taken with food. Once the medication dispenser unit 30 has been loaded with dispensing cups 46, and the dispensing program has been loaded into its controller 58, and activated via the keypad 66, a patient alert will be generated by the light 81 indicating to the patient when each dispensing time occurs for a prescribed medication dosage. Prior to the alert light 81 being activated, the particular one of the tubes 70 which has, as its lowermost dispensing cup 46, the cup having the medication to be taken at the alert time is rotated into alignment with the dispensing mechanism 72. As will be described in more detail with reference to FIGS. 5A and 5B, if the patient depresses the dispensing button 68, or the equivalent button 34 of FIG. 2, during the programmed time window the dispensing mechanism 72 is activated and that lowermost dispensing cup 46 is deposited into a chute 36 and thereby made accessible to the patient.

The FIG. 2 example on-site dispensing unit 30 has an emergency button 38 installed on it. As will be understood from the description below, when the emergency button 38 is depressed an emergency call is automatically placed to one or more remote sites, such as the caregiver 16 or the central monitoring facility 20.

FIG. 3 shows the medication dispenser 30 with the access panel 42 open. With the access panel 42 open the manual program keypad 44 can be accessed. Loading individual medication canisters 46 is also accomplished with the access panel 42 open. Each dispensing tube 48 is exposed in turn to be loaded with the individual medication canister 46. Also, access to the missed medicine canisters 45 is provided when access panel 42 unlocked and open. Access panel 42 can be locked to prevent unwanted access to the missed medication and manual program keypad 44.

FIG. 4 shows an exploded view of the example on-site medication dispenser unit 30, wherein a dispenser tube carousel 50 having, for this example, a plurality of ten canister tubes 70 is connected to a drive gear 52 which is rotated by a motor 54 located in the base. The base 56 houses a controller 58 and a battery pack 62. The controller 58 can be one of several standard off-the-shelf microprocessor-based controllers having standard-type actuator or servo drive interfaces and detector inputs, such as, for example, Intel® 80C196KB 16 bit microcontroller device or equivalent.

The base 56 of the depicted example is also designed to accommodate an LCD display 64 and keypad 66 and a dispensing button 68, which is equivalent to the button 34 of FIG. 2.

The position of the carousel 50 is determined by a position detector 76 located under the carousel 50, which relays positional information to the controller 58. The positional information relayed to the controller 58 is used to determine which of he tubes 51 has the canister 46 having the medication dosage that is scheduled to be released according to a dispensing program entered by a caregiver through the keypad 66 or received from a remote source, such as the doctors office 6 shown in FIG. 1. The tube carousel 50 is protected against contaminants and tampering by the cover 78 which mates to the base 56 when installed over the tube carousel 50.

Each of the ten tubes 70 may contain up to six of the canisters 46, and the tubes may be loaded with the canisters 46 in a variety of different configurations in association with the dispensing schedule entered into the controller 58. For example, if a patient is to receive a first medication at noon, and a second medication twice daily, e.g., at eight in the morning and ten at night, then each day would require three canisters 46. Each of the tubes 70 could therefore conceivably hold two days of medication. The unit 30 could, depending on design choice, access two days in succession from one of the tubes 70 before rotating the carousel 50 to the next tube 70 or, alternatively, dispense three canisters 46 in a day from one tube 70, and then rotate to the next tube 70 for the next day, and repeat the cycle until all of the tubes 70 were completely emptied. Other variations are readily seen by one of ordinary skill in the art.

Figure 5A:
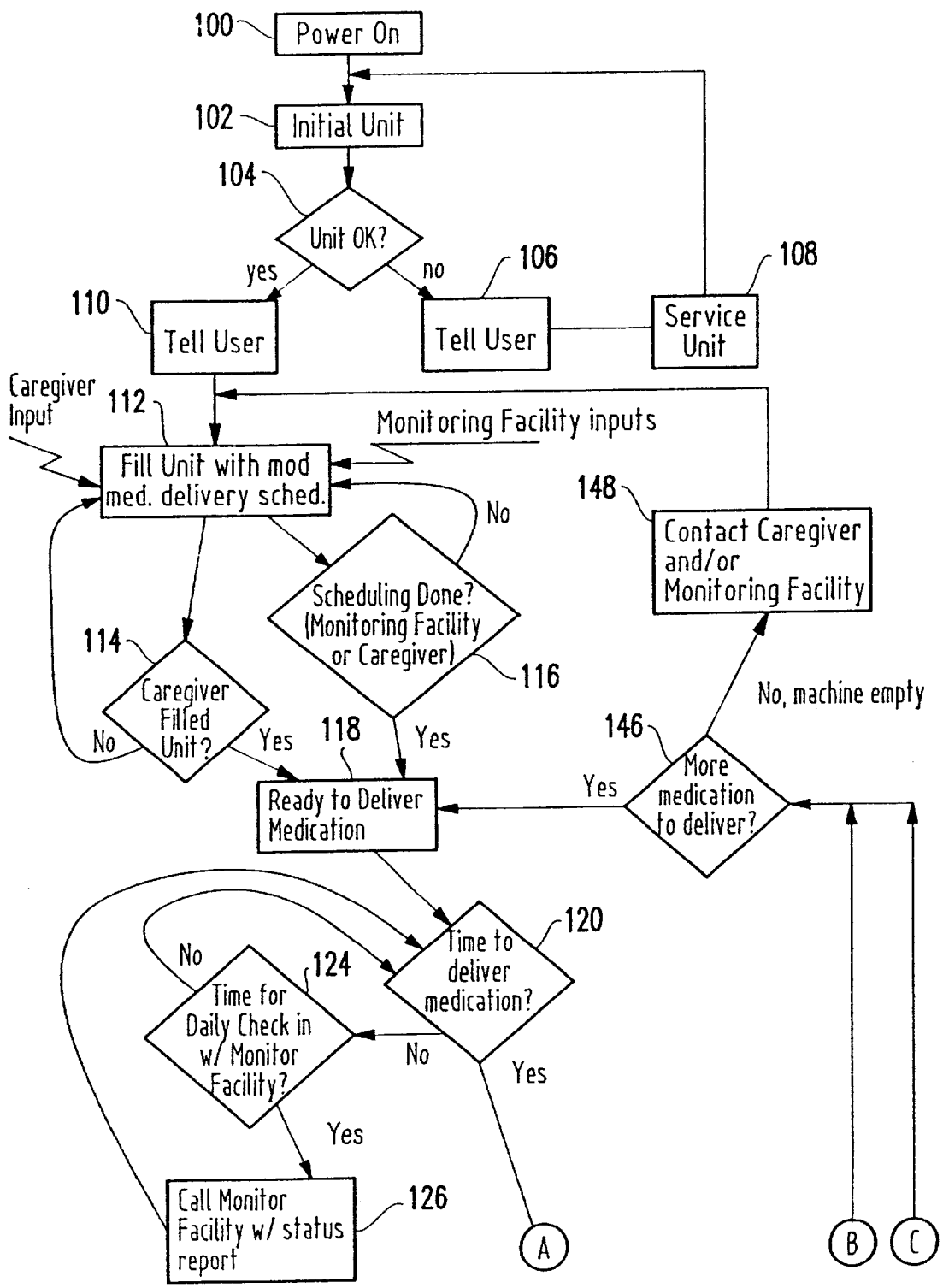

FIGS. 5A and 5B together depict an example high level operational flow chart of a first embodiment of a medication system as depicted by FIG. 1, with an on-site medication dispensing unit such as shown by FIGS. 2–4.

Referring to FIG. 5A, after power to the dispensing unit 2 is turned on at block 100, block 102 initiates an initializing process.

Initialization of the unit includes home positioning the tube carousel 50, home positioning the dispense mechanism 72, configuring the controller 58 hardware and embedded software performing built-in self tests, and informing the patient/caregiver of the successful completion of said initialization via pre-recorded voice message and LCD message 64.

After the initialization process decision, block 104 conducts a self-test operation. Self test of the unit includes the test of all controller 58 memory, loopback testing of the embedded controller 58 modem, battery 62 and power supply voltage measurements, and the carousel 50 and dispense mechanism 72 positioning sensor 76 and 82 calibration.

If the on-site medication dispensing unit 30 is not functioning properly, the user is notified in function block 106, the unit 30 is serviced (or replaced) in function block 108 and the process loops back to the start of the initialization process in block 102. If the unit is functioning properly the user, i.e., the caregiver operating the unit, is notified in function block 110. Next, at input block 112, the unit 30 is ready to be loaded with medication dosages by the caregiver and to receive medication dosage scheduling into its controller 58 on the circuit board assembly of FIG. 4, from either a remote source, such as the doctor's office 6 of FIG. 1, or by manual input from the caregiver through a keypad such as the assembly 66 of FIG. 4. An example data structure by which the controller 58 arranges the received medication dosage scheduling information is a linked list. Many other methods, such as push-pop or pointer-type stacked instructions, are readily identified and implemented by one of ordinary skill in the art. Decision block 114 determines if the unit 2 is filled. If the unit 30 is not filled, the decision block 114 initiates a process loop back to block 112. Otherwise the medication is ready to dispense in function block 118, subject to decision block 116 which determines if the medication dosage schedule has been input into the controller 58 on the printed circuit board assembly 58 of FIG. 4. If the schedule has not been input, the decision block 116 initiates a process loop back to function block 112. Otherwise the medication is ready to dispense in function block 118.

Decision block 120 is carried out by the controller 58 executing conventional timer-based commands (not numbered) in accordance with the loaded dispensing schedule, and determines if it is time to deliver a medication according to that schedule.

If the answer at block 120 is "no", decision block 124 determines whether it is time to check in with the central monitoring facility 20. The specific times and frequencies for such check are entered, for example, with the dispensing schedule at step 116. If it is time to check in with the monitoring facility 20, a call is initiated as shown in function block 126, otherwise a process loop is initiated back to decision block 120. The call is made via, for example, the patient's phone 14 shown in FIG. 1.

If the answer at block 120 is "yes", the patient is alerted, as shown by the FIG. 5B function block 122, by a first level attention getting signal (not shown). The attention getting signal may be an audible sound through a speaker 80 associated with the unit 30 and/or by a visible light signal emanated by a light emitting device 81 associated with and/or mounted to the unit 30. Additionally, a pre-recorded voice message is played by the unit.

Concurrent with the start of the first level attention getting signal at block 122, the controller at block 132 begins to measure the time that elapses until the patient presses the button 34. If the button 34 (68 in FIG. 4) is pressed prior to the first time limit, the selected canister is delivered through the chute 36 (74 in FIG. 4) to the patient. For this example the dispensing schedule is a linked list (not shown). The next dose to be dispensed is at the "top" of the list. The delivery time field (not shown) of the dispensing information is used by the on-board clock (not shown) of the microcontroller 58 to sequence through the linked list. Each time a medication canister cup is dispensed, its contained medication dose is "delivered" and the microcontroller 58 removes it from the linked list. The next dose in the list then becomes the "active" element.

If a first attention getting time expires and the patient has not yet pressed the button 34, a second level alert is initiated in block 134, otherwise the first level alert remains active in block 122. The second attention-getting signal generated at block 134 is either a louder or changed frequency audible sound, a brighter light, louder and/or a more urgent pre-recorded message, or a combination of the three.

Decision block 135 detects whether or not the patient has pressed the delivery button 34, while block 136 determines if a second level attention getting time has expired prior to such detection. If the button 34 is pressed prior to the second level attention getting time expires, the process goes to block 130 and the medication canister is dispensed through the chute 36 and, as stated above, the dispensing entry corresponding to the dispensed canister is removed from the list.

If the second level attention-getting time has expired, the medication is placed in an internal safe container, as shown by block 138, and the second level alert is deactivated.

After the medication is placed in the internal safe container 83, as shown by function block 138, a call is initiated to the primary caregiver, as shown by block 140. Referring to FIG. 1, the call by function block 138 is placed through, for example, the patient's phone 14. As to the identity of the primary caregiver, this could be the retirement home programming/monitoring facility 12 shown in FIG. 1 or, if the on-site unit is located in a private home, it could be the telephone 16 of designated primary care person, such as a relative or a private nurse.

Referring to FIG. 5A, decision block 142 determines how many calls will be attempted to the primary caregiver. If the preset amount of call attempts is exceeded without contacting the primary caregiver, function block 144 initiates a call to a second caregiver. Caregiver contact is complete when the caregiver depresses the appropriate telephone key after hearing the pre-recorded voice message enunciated over the telephone by the unit. If, on the other hand, the primary caregiver is contacted decision block 142 is satisfied and prepares for the delivery of the dose, decision block 146. Decision block 146 in FIG. 5A determines if the unit is empty of medication dosages. If the unit is empty the process goes to block 148 and a caregiver is contacted and the process loop returns to the start of the medication filling process in block 112; otherwise the process loop returns to the ready to dispense medication mode in block 118.

As discussed above, if the primary caregiver is not successfully contacted, a call to a second caregiver is initiated in block 144. FIG. 1 does not separately depict a second caregiver, as this would be, for example, simply another caregiver and caregiver's phone such as item 16. Decision block 150 determines how many calls will be attempted to the second care giver. If the preset programmable amount of call attempts is exceeded without contacting the second caregiver, an attempt will be made to call a third caregiver in function block 152. Decision block 154 then determines how many calls will be attempted to the third care giver. If the preset amount of call attempts is exceeded without contacting the third caregiver, an attempt will be made to call a fourth caregiver, as shown at function block 156. Decision block 158 determines how many calls will be attempted to the fourth care giver. If the preset amount of call attempts is exceeded without contacting the fourth caregiver, an emergency facility or a central monitoring facility, such as the monitoring facility 20 shown in FIG. 1, will be contacted in function block 160. After the emergency or central monitoring facility is contacted the process loop goes to decision block 146.

As shown by FIG. 5A, if a caregiver is contacted at anytime during the missed medication mode the process loop goes to decision block 146.

The above-described embodiment generates an audible or other human-detectable signal at step 132, alerting the patient that it is time to press the button 68. Alternatively, the controller 58 can be programmed to allow a specific time window during which the medication may be dispensed such as, for example, a time window that straddles a nominal dispensing time of one o'clock PM. An example time window straddling one o'clock PM would be from 12:45 PM to 1:15 PM. If the patient presses the dispensing button 68 during that time window the medication is dispensed as described above. If the patient does not press the button 68 then, in accordance with this example embodiment, the selected canister 46 containing the medication scheduled for dispensing at the programmed time is placed in the missed dose compartment. Also in accordance with this embodiment, if the patient does not press the button 68 within the time window the controller 58 becomes unresponsive to the button 68 until the next time window.

Figure 6A:
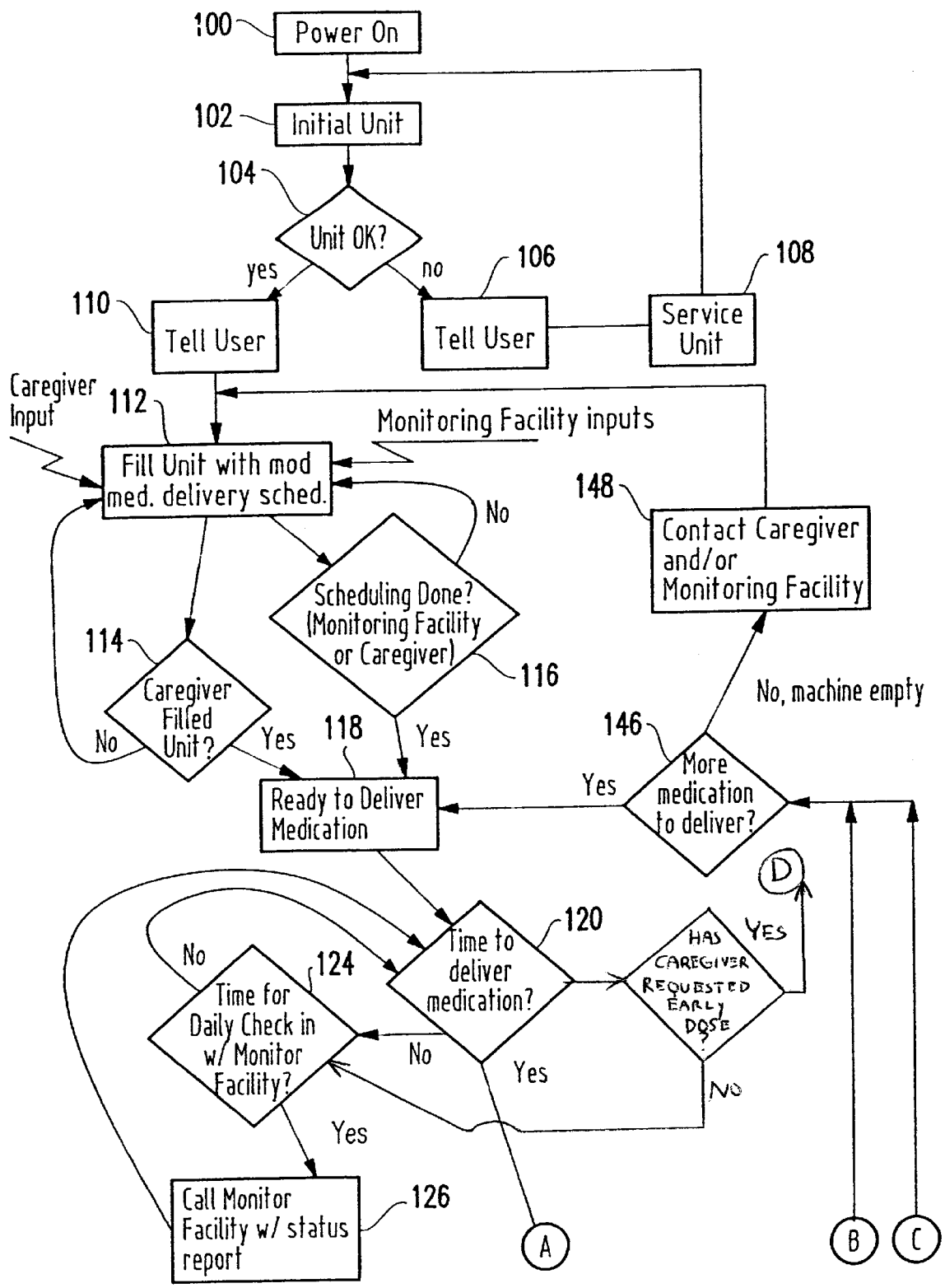

Referring to FIGS. 6A and 6B a still further embodiment of this invention comprises an early-dosing feature, which permits authorized caregivers to override or step through the dispensing schedule and obtain dispensing of all medications that, according to the dispensing regimen programmed into the controller 58, were to be dispensed over selectable time period. For example, there may be a need to take the patient for an eight hour excursion to a location where alternative sources for, or authorization, for the patient's medication are not available. This further embodiment accommodates such situations. More particularly, additional software code is pre-loaded into the programmable controller 58 which enables an authorized caregiver to enter an early dispense command, either by a dedicated button or typed command.

Referring to FIGS. 6A and 6B, the early dosing feature will now be described. Functional blocks of FIGS. 6A and 6B having like numbers as shown at FIGS. 5A and 5B are identical and, accordingly, will not be described again except where necessary to understand the early-dosing features of this embodiment. Referring to FIG. 6A, block 120 identifies whether or not it is time to deliver medication in accordance with the regimen loaded into the programmable controller 58 at block 112. As described in reference to FIGS. 5A and 5B above, the answer at block 120 is "yes" then the process goes to block 122 and generates the first level alert signal. For this embodiment, however, if the answer at block 120 is "no" the process goes to block 200 to check if the caregiver has entered a request for an early dose. In other words, blocks 120 and 200 continuously loop to poll the manual program keypad 44 until either the time to deliver the medication occurs or the caregiver enters a command for early dosing, whichever occurs first. If the answer at block 200 is "yes", the process goes to block 130 and delivers the medication to the user as described above. As stated for the first described embodiment, the controller 58 maintains the dispensing schedule as a linked list and, therefore, concurrent with the dispensing operation of block 130, the associated dispensing entry is removed from the list.

For this example embodiment the entry of a command for early dosing would only dispense one future dose of the medication to be dispensed. If the caregiver wants an early dispensing of more than one dose of medicines he or she restarts the above-described early dose function. They can do this as many times as there is medication in the machine.

Figure 8:
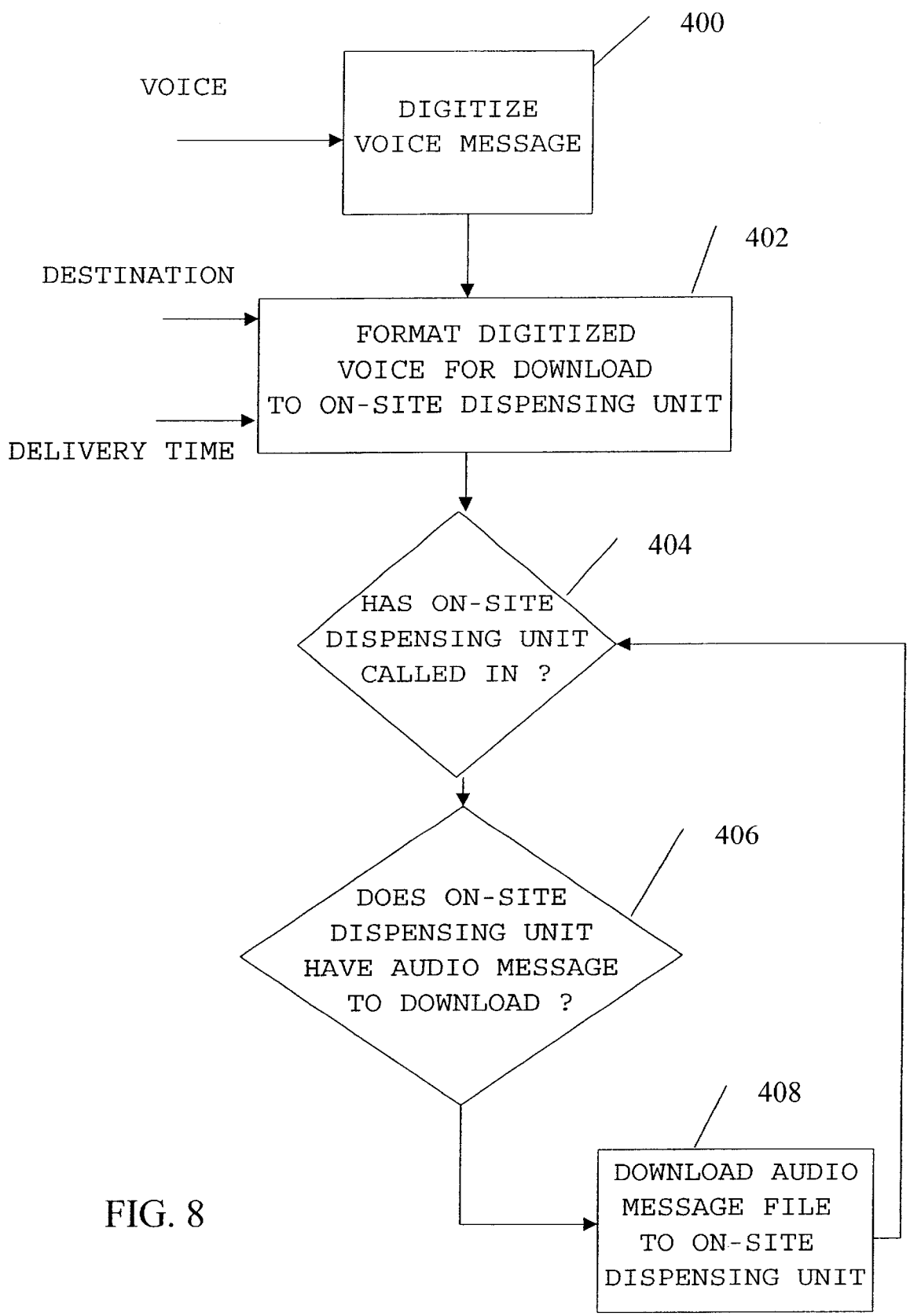
FIG. 8 is a lower-level operational flow chart of an audio messaging feature of the embodiment of FIGS. 7A and 7B.

Referring to FIGS. 7A 7B and 8, a still further embodiment of the invention comprises a messaging feature combined with, for this example, the early-dosing feature of FIGS. 6A and 6B. The additional hardware required for this messaging feature comprises a conventional microphone, A/D converter and data formatting unit connected, or installed into, the computer located at the central monitoring facility, and a speaker and speaker driver circuitry installed on the on-site dispensing unit. Regarding the central monitoring facility, most commercially available PC-type workstations can be equipped with a built-in microphone with A/D capabilities, commonly referred to as a "sampler". An example system would be a standard PC with a Rockwell® AK28-D440-041 Voice/Fax/Modem card, which features an A/D converter and an analog microphone input, installed. One of several commercially available microphones, such as a Telex Voice Commander® Computer Microphone, is then plugged into the audio input port of the example Rockwell card.

Functional blocks of FIGS. 7A and 7B having like numbers as shown at FIGS. 5A, 5B, 6A and 6B are identical and, accordingly, will not be described again except where necessary to understand the audio messaging feature of this embodiment.

Referring to FIGS. 7A, 7B and 8, an example of the messaging feature of this embodiment will be described. First, referring to FIG. 8, at block 300, an audio or spoken voice message is input to a microphone (not shown) installed in, or connected to the personal computer (PC) or workstation (not shown) of the central monitoring station and A/D converted or digitized. Example spoken voice messages include: "It is now flu season, you should get your flu shot" and "Don't forget, Mrs. Smith, that you have a doctor's appointment his Friday at 3 o'clock in the afternoon." The process then goes to block 402 where the digitized voice message is formatted into an industry standard digital audio format, such as Intel HEX, for download to one or more designate ones of the above-described on-site dispenser units. Also at block 402 the user at, for this example, the central monitoring facility, enters a DELIVERY TIME command, specifying the time at which the on-site dispensing unit is to broadcast the message, and a DESTINATION command, specifying which on-site dispensing unit(s) the message is to be downloaded to for playing. The DELIVERY TIME and DESTINATION commands are, for this example, included as a header (not numbered) of the formatted voice message. Next, at block 404 the process being executed at the central monitoring station waits for an on-site dispensing unit call in. Referring to FIG. 7A, the call in, for this example, is the routine status call-in described at block 126 of the embodiments above, with the jump-off to FIG. 8 labeled as "E". When a call in is detected the process goes to block 406 to determine if the particular on-site dispensing unit is the unit, or one of the units, specified by the DESTINATION command entered at block 402. If the answer is "no" the process loops back to block 404 and waits for the next call in from an on-site dispensing unit. If the answer at block 406 is "yes" the process goes to block 408 and downloads the voice message. The operation carried out by the controller 58 of the on-site dispensing unit in receiving and downloading the voice message will be described in reference to FIGS. 7A and 7B.

Referring to FIGS. 7A and 73, the voice message receive, download, and play operation of the on-site dispensing unit will be described. For purposes of this description, the voice messaging feature is described as being in combination with the early dosing feature of FIGS. 6A and 6B. Accordingly, like numbered blocks have like functions and will not be discussed again except where necessary for understanding the invention. Referring to block 124 at FIG. 7A, at this step of the process, as described for FIG. 5A, the controller 58 determines if it is time to check in with the central monitoring facility. If the answer is "no" the process loops back to block 120 to determine if its time to deliver a medication dose, as described above. If the answer at block 124 is "yes" the process goes to block 126 and proceeds to connect to the central monitoring facility. For the example described above the connection is made via telephone modem (not shown). In the present embodiment the controller 58, in addition to reporting its status information as described above, checks at block 500 with the central monitoring facility to determine if there is an audio message for that controller's dispensing unit, that decision being dependent on the information input in the voice message input receiving steps described in reference to FIG. 8. If the answer at block 500 is "no" the process loops back to block 120 to determine of it is time to deliver a canister of medication. However, if the answer is "yes" the process goes to block 502, downloads the audio message, including the header having the playback time (or other event triggering playback) and loops back to the same block 120 to check whether it is time to execute the above-described dispensing steps.

After looping back to block 120, by any of the paths shown at FIG. 7A and, if it is not yet time to dispense a canister the process goes to block 200 and checks as to whether an early-dosing command has been input, as described above. If the answer is "no" the process continues to block 504 and checks to determine if it time to retrieve and playback the audio message. If it is time the controller goes to block 506, retrieves the message, and plays it through the speaker (not shown). If block 504 determines that it is not to playback an audio message, or if there is no message, the process again loops back to block 120. In this manner the controller 58 continuously polls the manual program keypad 44 in a continuous loop until either the time to deliver the medication occurs, causing a "yes" at block 120 and resulting jump labeled as "A" to the alerting step 122, or the caregiver enters a command for early dosing, whichever occurs first, causing a jump labeled as "D" to the dispensing step 130 of FIG. 7B, or the time is that specified by the DELIVERY TIME command described above, causing a "yes" at block 504, whereupon the process goes to step 506 to retrieve and play the spoken voice message downloaded at step 408.

While the invention has been described in terms of its preferred embodiments, those skilled in the art will recognize that the invention can be practiced with modification within the spirit and scope of the appended claims. For example, the second level attention getting signal, shown in block 134 of the process depicted in FIG. 5A, could be omitted.

As another example variation of the described invention, it is described above, referring to FIGS. 5A and 5B, that the computer 58 rotates the carousel 50 to place one of the tubes 70 into a proper dispensing position for dispensing its container 46 before the button 68 is pressed, based on an upcoming dispensing schedule requirement which the controller 58 reads from its memory (not numbered). Then when the dispensing button 68 is depressed, at the prescribed time, the carousel 50 is already in the correct position and the dispensing mechanism 72 is operated to dispense the container 46 having the scheduled dosage from the selected tube 70 into a chute 74 formed in the base 56. As an alternative to this pre-positioning of the carousel 50, the controller 58 can be programmed such that upon pressing the button 68 the carousel 50 is directly rotated to position an individual one of the tubes 70, into an operative relation to the dispensing mechanism 72.

We claim:

1. A medication dispensing system, comprising:
    a digital data communication network;
    a central monitoring station connected to said digital data communication network;
    means for retrievably storing an audio message and for outputting an audio signal to said digital data communication network representing the stored audio message; and
    an on-site medication dispensing unit, located remote from said central monitoring station, comprising:
        a controller, having means for communicating through said digital data communication network with said central monitoring station, means for retrievably storing a dispensing schedule information, and means for retrievably storing a communication receiving address of a first caregiver and a communication receiving address of a second caregiver;
        a plurality of canisters for storing pills;
        canister support means for supportably holding said canisters;
        a main enclosure means for enclosing said canister support means, said main enclosure means having a movable access cover, and having a canister dispensing port, said access cover movable to an open position for manually placing said canisters into said canister support means, and movable to a closed position for preventing manual access to said canisters;
        means for generating a dispensing notification signal detectable by human senses based on said dispensing schedule;
        a human interface means for receiving a manually entered dispense request signal;
        means for selecting a canister from among said canisters within said canister support means based on said dispensing schedule information and for dispensing said selected canister through said canister dispense port in response to receipt of said dispense request signal within a first predetermined time after generation of said dispensing notification signal;
        means for detecting a failure to receive the manually entered dispense request signal before a lapse of said first predetermined time after said generation of said dispensing notification signal;
        means for transmitting a first alarm call in accordance with said stored communication receiving address of said first caregiver receiver in response to said detecting a failure;
        means for receiving a first confirmation signal from said first caregiver;
        means for detecting a failure to receive said first confirmation signal before a lapse of a second predetermined time after said transmitting a first alarm call to said first caregiver receiver;
        means for transmitting a second alarm call in accordance with said communication receiving address of said second caregiver receiver based on said detecting a failure to receive said first confirmation signal; and
        means for receiving and retrievably storing said audio signal representing the stored audio message, having means for generating an audible message corresponding to said stored audio signal.

2. A medication dispensing system according to claim 1, wherein said on-site medication dispensing unit further comprises:
    a missed dose enclosure means for holding at least one of said canisters in a manually inaccessible manner, said missed dose enclosure means having a canister input port; and
    means for placing said selected canister through said canister input port into said missed dose enclosure means in response to a lapse of said first predetermined time after generation of said dispensing notification signal without receipt of said dispense request signal.

3. A medication system according to claim 1, wherein said means for retrievably storing an audio message and for outputting an audio signal representing the stored audio message further comprises means for receiving an external signal defining a message initiation event, and
    wherein said on-site medication dispensing system further comprises means for detecting an event corresponding to said external signal's definition of an iinitiation event, and wherein said means for receiving and retrievably storing said audio signal representing the stored audio message retrieves said stored audio message and generates said audible message in response to said detecting said event.

4. A medication system according to claim 1, wherein said on-site medication dispensing unit further comprises means for entering an early dosing command data, and wherein means for selecting a canister and for dispensing said selected canister through said canister dispense port performs said operations in response to any one of:
  (i) receipt of said dispense request signal within a first predetermined time after generation of said dispensing notification signal, and
  (ii) receipt of said early dosing command.

5. A medication dispensing system, comprising:
a digital data communication network;
a central monitoring station connected to said digital data communication network; and
an on-site medication dispensing unit, located remote from said central monitoring station, comprising:
  a controller, having means for communicating through said digital data communication network with said central monitoring station, means for retrievably storing a dispensing schedule information, and means for retrievably storing a communication receiving address of a first caregiver and a communication receiving address of a second caregiver;
  a plurality of canisters for storing pills;
  canister support means for supportably holding said canisters;
  a main enclosure means for enclosing said canister support means, said main enclosure means having a movable access cover, and having a canister dispensing port, said access cover movable to an open position for manually placing said canisters into said canister support means, and movable to a closed position for preventing manual access to said canisters;
  means for generating a dispensing notification signal detectable by human senses based on said dispensing schedule information;
  a human interface means for receiving a manually entered dispense request signal;
  means for entering an early dosing command data;
  means for selecting a canister from among said canisters within said canister support means, based on said dispensing schedule information, and for dispensing said selected canister through said canister dispense port in response to any one of:
    (i) receipt of said dispense request signal within a first predetermined time after generation of said dispensing notification signal, and
    (ii) receipt of said early dosing command;
  means for transmitting a first alarm call to a first caregiver receiver, in accordance with said stored receiving address of said first caregiver, based on said detecting a failure and an absence of said early dosing command;
  means for receiving a first confirmation signal from said first caregiver;
  means for detecting a failure to receive said first confirmation signal before a lapse of a second predetermined time after said transmitting a first alarm call to said first caregiver receiver; and
  means for transmitting a second alarm call to a second caregiver receiver, in accordance with said stored receiving address of said second caregiver, based on said detecting a failure to receive said first confirmation signal and an absence of said early dosing command.

6. A medication dispensing system according to claim 5, wherein said on-site medication dispensing unit further comprises:
  a missed dose enclosure means for holding at least one of said canisters in a manually inaccessible manner, said missed dose enclosure means having a canister input port; and
  means for placing said selected canister through said canister input port into said missed dose enclosure means in response to a lapse of said first predetermined time after generation of said dispensing notification signal without receipt of said dispense request signal.

7. A method for dispensing medication, comprising:
storing a digitized voice message within a central data server;
transmitting said digitized voice message to a digital storage in a remote medication dispenser;
inserting pills into a plurality of canisters for storing pills;
inserting said canisters into an enclosure of said remote medication dispenser, said enclosure having a canister dispense port;
storing a dispensing program in a controller associated with said remote medication dispenser;
storing a first caregiver receiving address data in said controller;
storing a second caregiver receiving address data in said controller;
generating a dispense notification alarm detectable by human senses based said dispensing program;
selecting a canister from among said canisters within said enclosure based on said dispensing program;
in response to said remote medication dispenser receiving a manually entered dispense request signal within a first predetermined time after generation of said generating a dispense notification alarm performing the following step:
  dispensing said selected canister through a canister dispense port;
in response to failing to receive said manually entered dispense request signal within said first predetermined time after generation of said dispensing performing the following step:
  transmitting a first alarm call to a first caregiver, in accordance with said first caregiver receiving address data;
in response to failing to receive a manually entered dispense request signal within a second predetermined time after said transmitting said first alarm call performing the following step:
  transmitting a second alarm call to a second caregiver receiver, in accordance with said second caregiver receiving address data; and
retrieving said voice message from the storage of said remote medication dispense unit and broadcasting an audio message from a speaker proximal to said remote medication dispense unit representing said retrieved voice message.

8. A method for dispensing medication according to claim 7 further a step of entering an early dosing command data, and wherein said step of dispensing said selected canister through a canister dispense port is performed in response to any one of:
- (i) receipt of said dispense request signal within a first predetermined time after generation of said dispensing notification signal, and
- (ii) receipt of said early dosing command data.

9. A method according to claim 7, comprising a further step of:

in response to a lapse of said first predetermined time after said generating of said dispensing notification signal without receipt of said dispense request signal, placing said selected canister into a missed dose enclosure, said missed dose enclosure being manually accessible through a lockable access door.

10. A method according to claim 8, comprising a further step of:

in response to a lapse of said first predetermined time after said generating of said dispensing notification signal without receipt of said dispense request signal, placing said selected canister into a missed dose enclosure, said missed dose enclosure being manually accessible through a lockable access door.

* * * * *